US008597663B2

(12) United States Patent
Monteiro et al.

(10) Patent No.: US 8,597,663 B2
(45) Date of Patent: Dec. 3, 2013

(54) **POLYSACCHARIDE IMMUNOGENS FROM *CLOSTRIDIUM DIFFICILE***

(75) Inventors: Mario Artur Monteiro, Guelph (CA); Jeyabarathy Ganeshapillai, Scarborough (CA); Nagalingham Ganeshapilla, legal representative, Scarborough (CA); Mononmanydevi Ganeshapilla, legal representative, Scarborough (CA)

(73) Assignee: University of Guelph, Guelph, Ontario (CA)

( * ) Notice: Subject to any disclaimer, the term of this patent is extended or adjusted under 35 U.S.C. 154(b) by 589 days.

(21) Appl. No.: 12/676,369

(22) PCT Filed: Sep. 11, 2008

(86) PCT No.: PCT/CA2008/001593
§ 371 (c)(1),
(2), (4) Date: Aug. 31, 2010

(87) PCT Pub. No.: WO2009/033268
PCT Pub. Date: Mar. 19, 2009

(65) Prior Publication Data
US 2010/0330125 A1    Dec. 30, 2010

Related U.S. Application Data

(60) Provisional application No. 60/971,411, filed on Sep. 11, 2007.

(51) Int. Cl.
*A61K 39/00* (2006.01)
*A61K 39/38* (2006.01)
*A61K 39/02* (2006.01)
*A61K 39/08* (2006.01)

(52) U.S. Cl.
USPC ............. 424/247.1; 424/234.1; 424/239.1; 424/236.1; 424/184.1

(58) Field of Classification Search
None
See application file for complete search history.

(56) References Cited

U.S. PATENT DOCUMENTS

| | | | |
|---|---|---|---|
| 6,573,245 B1 | 6/2003 | Marciani | |
| 8,337,832 B2 * | 12/2012 | Kopecko et al. | 424/93.2 |
| 2004/0180850 A1 | 9/2004 | Natunen et al. | |
| 2007/0065461 A1 | 3/2007 | Guerry et al. | |
| 2010/0239600 A1 * | 9/2010 | Bigio et al. | 424/193.1 |
| 2010/0330125 A1 * | 12/2010 | Monteiro et al. | 424/247.1 |
| 2013/0078278 A1 * | 3/2013 | Kopecko et al. | 424/234.1 |

FOREIGN PATENT DOCUMENTS

| | | |
|---|---|---|
| WO | 96/40795 | 12/1996 |
| WO | 2007/038122 | 4/2007 |
| WO | WO 2009/033268 A1 * | 3/2009 |

OTHER PUBLICATIONS

Bertolo et al, Varbohydrate Research, Jun. 1, 2012, 354:79-85.*
Adamo et al, ACS Chem. Biol., 2012, 7:1420-1428.*
Cappelletti et al, Glycoconjugate Journal, Jul. 2011, 28/5: pp. No. 173 (abstract only).*
Porro et al, Molecular Immunology, 1985, 22/8:907-919.*
Costantino et al, Vaccine, 1992, 10/10:691-698.*
Ada et al, Clin Microbiol Infect 2003; 9: 79-85.*
Hofstad, T., "Virulence Factors in Anaerobic Bacteria", Eur. J. Clin. Microbiol. Infect. Dis., 1992, vol. 11, No. 11, pp. 1044-1048.
Ganeshapillai, J et al., "*Clostridium difficile* Cell Surface Polysaccharides: Towards a Carbohydrate-Based Vaccine" ASM 107th General Meeting, Toronto, Canada, vol. 107, Jan. 1, 2007, poster.
MacNair, J et al., "Alignment of absolute and relative molecular size specifications for a polyvalent penumococcal polysaccharide vaccine", Biologicals 33 (2005) 49-58.
Wenger, J.D., "Serogroup B Meningococcal Disease", Jama, 1999, vol. 281, No. 16, pp. 1541-1543.
Wilkins, T.D., and Lyerly, D.M., "*Clostridium difficile* Testing: after 20 Years, Still Challenging", J. of Clinical Microbiology, 2003, vol. 41, No. 2, pp. 531-544.
Kyne, L. et al., "Health care costs and mortality associated with nonsocomial diarrhea due to *Clostridium difficile*", Clin. Infect. Dis., 2002, vol. 34, pp. 346-353.
Ganeshapillai J et al., "Cell-Surface Polysaccharides of *Clostridium difficile*" Lisbon 2007.
Ganeshapillai J et al., "*Clostridium difficile* Cell-Surface Polysaccharides: Towards a Carbohydrate-Based Vaccine" Abstracts of the General Meeting of the American Society of Microbiology, 2007, p. 232.
Poxton, I et al., "Immunochemistry of the Cell-Surface Carbohydrate Antigens of *Clostridium difficile*" Journal of General Microbiology, 1982, vol. 128, pp. 1365-1370.
Ganeshapillai J et al., "*Clostridium difficile* cell-surface polysaccharides composed of pentaglycosyl and hexaglycosyl phosphate repeating units", Carbohydrate Research, 2008 vol. 343, pp. 703-710.
Pepin, J., et al., "*Clostridium difficile*-associated diarrhea in a region of Quebec from 1991 to 2003: a changing pattern of disease severity", CAMJ., 2004, vol. 171, No. 5, pp. 466-472.
Anderson, P., "Antibody Responses to Haemophilus influenzae Type b and Diphtheria Toxin Induced by Conjugates of Oligosaccharides of the Type b Capsule with Nontoxic Protein CRM(197)", Infect. and Immun., 1983, vol. 39, No. 1, pp. 233-238.

* cited by examiner

*Primary Examiner* — Nita M Minnifield
(74) *Attorney, Agent, or Firm* — Bereskin & Parr LLP; Melanie Szweras

(57) ABSTRACT

The application relates to *Clostridium difficile* cell surface polysaccharides, compositions comprising *Clostridium difficile* cell surface polysaccharides, and includes kits, methods and uses thereof.

21 Claims, 8 Drawing Sheets

A)

B)

A)

...→6)-Glc-(1→P→4)-Rha-(1→...

B)

...→3)-Man-(1→P→6)-Glc-(1→...

A)

B)

US 8,597,663 B2

POLYSACCHARIDE IMMUNOGENS FROM *CLOSTRIDIUM DIFFICILE*

This application is a National Stage of co-pending International Application No. PCT/CA2008/001593, filed Sep. 11, 2008, which claims the benefit of U.S. Provisional Patent Application No. 60/971,411, filed Sep. 11, 2007, the contents of both of which are herein incorporated by reference.

The present application relates to novel immunogenic cell surface polysaccharides and methods and uses thereof.

BACKGROUND OF THE APPLICATION

*Clostridium difficile* is a Gram-positive bacterium that is known to be the cause of enteric diseases. It is the leading cause of antibiotic-associated diarrhea and pseudomembranous colitis (Knoop, F. C.; Owens, M.; Crocker, I. C.; *Clin. Microbiol. Rev.* 6, 1993, 251-265). The frequency and severity of outbreaks associated with *C. difficile* has increased in recent years (Pepin, J.; Valiquette, L.; Alary, M. E.; Villemure, P.; Pelletier, A.; Forget, K.; Pepin, K.; Chouinard, D.; *JAMC.* 171, 2004, 466-472). Most ingested vegetative *C. difficile* cells are destroyed by the acidic environment present in the stomach. Spores, however, can survive this feat and upon exposure to bile acids can germinate in the small bowel. The decreased levels of normal microbial cells in the intestines due to medical treatments such as antibiotics use and chemotherapy, allow *C. difficile* to proliferate.

In humans, *C. difficile*-associated diarrhea (CDAD) is the most commonly diagnosed cause of hospital-associated and antimicrobial-associated diarrhea. Risk of CDAD has traditionally been higher among elderly patients and those that have undergone hospitalization, gastrointestinal surgery or were exposed to antibiotics. In the United States, the estimated number of cases of *C. difficile*-associated disease exceeds 250,000 per year (Wikkins T D and Lyerly D M, 2003, J. Clin Hasp Infect 48:81), with total additional health care costs approaching US $1 billion annually (Kyne L, et al., 2002, Clin Infect Dis 34:346-353).

In the past five years an unexpected increase in the incidence of CDAD has been observed. This has also been associated with higher rates of severe CDAD, treatment failure and death. Severe cases are being more frequently identified in younger patients and those without traditional risk factors. Much of this change has been associated with international dissemination of an outbreak clone, designated ribotype 027 (also known as North American pulsotype 1 (NAP1) and BI). Prevention of *C. difficile* is based on patient isolation, improved sanitation, improved infection control and antimicrobial restriction, all of which are associated with high healthcare costs. In addition, prophylactic use of antibiotics has been used for the prevention of infection; however, it led to an increase in the incidence of disease. Treatment of *C. difficile* infections is also problematic since the response to metronidazole, the main first-line treatment, is becoming unpredictable. Vancomycin, the alternative choice, is expensive and its use raises concern about emergence of vancomycin-resistant enterococci and other vancomycin-resistant organisms.

CDAD is also an important problem in many animal species such as horses and pigs. It may also be a cause of disease in other species. There is concern that *C. difficile* may be transmissible from animals to humans because the types of *C. difficile* isolated from animals are often the same as those found in people, including the outbreak strain ribotype 027. This concern has increased based on the finding of *C. difficile* in retail meat samples.

The reported increasing incidence of CDAD, its recurrence rates, and its impact on morbidity and mortality, as well as the costs associated with treatment and appropriate isolation procedures to limit its spread make clear the need for effective prevention approaches of CDAD.

One particular strain, designate ribotype 027 or NAP1 has emerged as an important cause of sporadic and epidemic disease internationally. Serious outbreaks with high morbidity, high mortality, poor response to treatment and high relapse rates have been reported. This strain produces 3 main toxins: toxin A, toxin B and CDT (binary toxin). It also has a deletion in a purported toxin regulating gene that appears to increase toxin production, at least in vitro (Just, I.; Selzer, J.; Wilm, M.; von Eichel-Streiber, C.; Mann, M.; Aktories, K.; *Nature.* 375, 1995, 500-5033). This spore-forming bacterium is found to resist phagocytosis by cell surface polysaccharides.

Poxton and Cartmill (Poxton, I. R; Cartmill; T. D. *J Gen Microbiol.* 1982, 128, 1365-1370) described the sugar composition of two preparations extracted from *C. difficile* strain NCTC 11223. The material obtained by NaOH treatment of cells was observed to contain glucose, mannose, galactosamine and phosphate, and the other, extracted by phenol treatment of cells, contained glucose, glucosamine, phosphate and fatty acids. In the same work, it was also observed that both preparations cross-reacted with *Clostridium sordellii* antiserum.

There is a growing need to develop a vaccine for humans and animals against *C. difficile* infection to prevent CDAD or prevent recurrence. Additionally, vaccination is needed in animals to prevent animal disease and to reduce shedding of *C. difficile* so as to reduce the risk of zoonotic transmission.

SUMMARY OF THE APPLICATION

The present application discloses novel *Clostridium difficile* cell surface polysaccharides including their covalent chemical structures and these novel polysaccharides are used in immunogenic compositions, in anti-*C. difficile* vaccine preparations and/or as diagnostic markers.

Accordingly, the present application includes isolated immunogenic *Clostridium difficile* cell surface polysaccharides.

In one embodiment, the cell surface polysaccharides comprise repeating pentasaccharide units of the formula I:

$$
\begin{array}{c}
\longrightarrow 4)\text{-}\alpha\text{Rha-}(1 \longrightarrow 3)\text{-}\beta\text{Glc-}(1 \longrightarrow \\
4)\text{-}\alpha\text{Glc-}(1 \longrightarrow 2)\text{-}\alpha\text{Glc-}(1 \longrightarrow P \\
3 \\
\uparrow \\
\alpha\text{Rha-}(1
\end{array}
\quad (I)
$$

wherein Rha is rhamnose, P is glycosyl phosphate and Glc is glucose or an immunogenic fragment thereof.

In another embodiment, the cell surface polysaccharides are compounds of the formula PS-I:

$$
\begin{array}{c}
[\longrightarrow 4)\text{-}\alpha\text{Rha-}(1 \longrightarrow 3)\text{-}\beta\text{Glc-}(1 \longrightarrow \\
4)\text{-}\alpha\text{Glc-}(1 \longrightarrow 2)\text{-}\alpha\text{Glc-}(1 \longrightarrow P]n \\
3 \\
\uparrow \\
\alpha\text{Rha-}(1
\end{array}
\quad (\text{PS-I})
$$

wherein n is an integer from 1 to 1000, Rha is rhamnose, P is glycosyl phosphate and Glc is glucose or an immunogenic fragment thereof.

In another embodiment, the cell surface polysaccharides comprise repeating hexasaccharide units of the formula II:

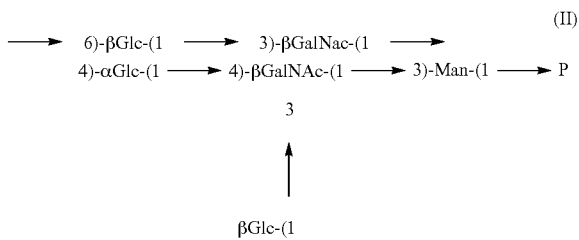

wherein Glc is glucose, GalNAc is N-acetyl-galactosamine, P is glycosyl phosphate and Man is mannose or an immunogenic fragment thereof.

In another embodiment, the cell surface polysaccharide are compounds of the formula PS-II:

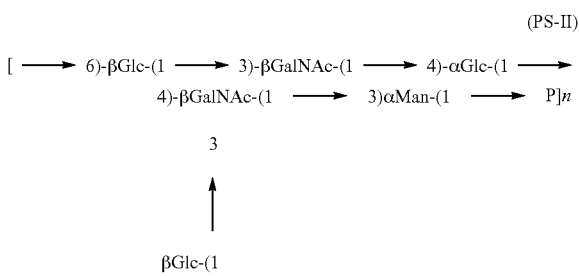

wherein, n is an integer from 1 to 1000, Glc is glucose, GalNAc is N-acetyl-galactosamine, P is glycosyl phosphate and Man is mannose or an immunogenic fragment thereof.

In another embodiment, the cell surface polysaccharides are compounds of the formula PS-III, which comprise glycerol (Gro), alditol phosphate (P), glucose (Glc), and N-acetylglucosamine (GlcNAc) within their covalent chemical structure.

Another aspect of the present application is a *Clostridium difficile* cell surface polysaccharide mixture comprising one or more *Clostridium difficile* cell surface polysaccharides.

Another aspect of the present application is an immunogenic composition comprising one or more *Clostridium difficile* cell surface polysaccharides.

A further aspect of the present application is a vaccine composition comprising one or more *Clostridium difficile* cell surface polysaccharides.

Another aspect of the present application is a kit comprising the cell surface polysaccharides disclosed herein or the cell surface polysaccharide mixture disclosed herein or the immunogenic compositions disclosed herein or vaccine compositions disclosed herein and instructions for use.

Another aspect of the present application is a method of inducing an immune response against *Clostridium difficile* in subject by administering to a subject in need thereof an effective amount of one or more of the cell surface polysaccharides disclosed herein or the immunogenic compositions disclosed herein or the vaccine compositions disclosed herein.

A further aspect of the present application is a method of treating or preventing *Clostridium difficile* infection in a subject by administering to a subject in need thereof an effective amount of one or more of the cell surface polysaccharides disclosed herein or the immunogenic compositions disclosed herein or the vaccine compositions disclosed herein.

An additional aspect of the present application is a method of treating or preventing *Clostridium difficile*-associated diarrhea in a subject by administering to a subject in need thereof an effective amount of one or more of the cell surface polysaccharides disclosed herein or the immunogenic compositions disclosed herein or the vaccine compositions disclosed herein.

The present application also discloses uses of the cell surface polysaccharides disclosed herein or the cell surface polysaccharide mixture disclosed herein or the immunogenic compositions disclosed herein or the vaccine compositions disclosed herein to induce an immune response against *Clostridium difficile* in a subject, to treat or prevent *Clostridium difficile* infection in a subject, and/or to treat or prevent *Clostridium difficile*-associated diarrhea in a subject.

A further aspect of the present application includes uses of the cell surface polysaccharides disclosed herein or the cell surface polysaccharide mixture disclosed herein or the immunogenic compositions disclosed herein or the vaccine compositions disclosed herein for the manufacture of a medicament to induce an immune response against *Clostridium difficile* in a subject, to treat or prevent *Clostridium difficile* infection in a subject, and/or to treat or prevent *Clostridium difficile*-associated diarrhea in a subject.

Other features and advantages of the present application will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE APPLICATION

I. Definitions

Figure 1:
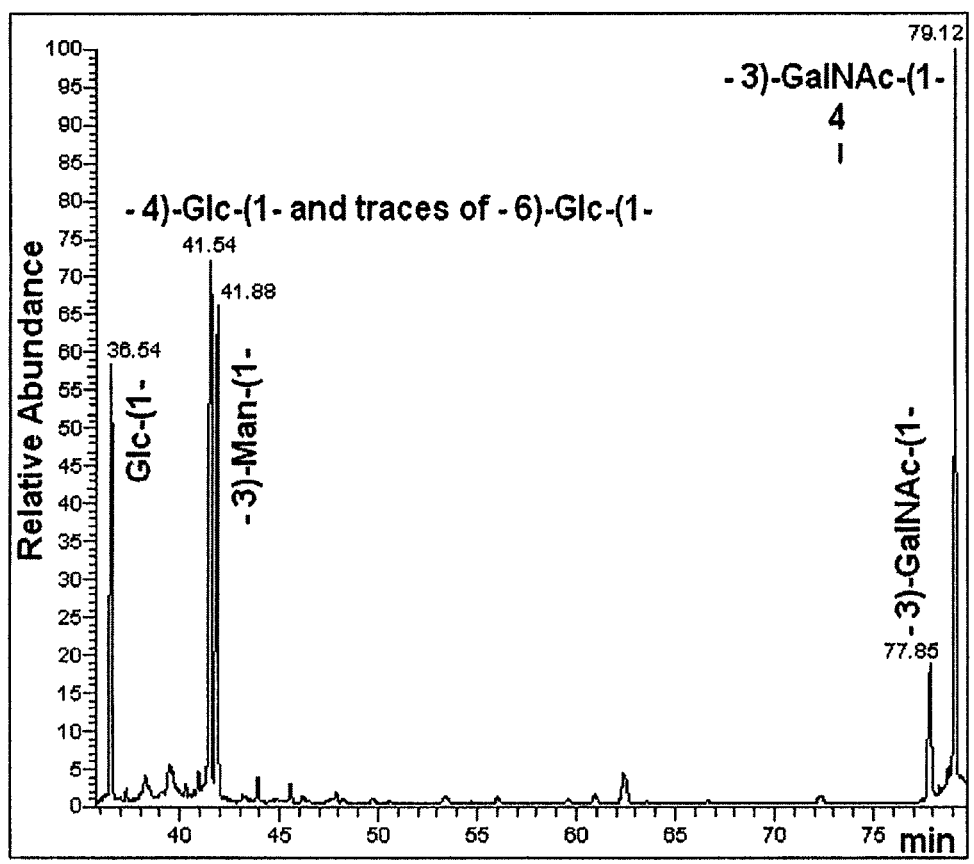
FIG. 1 is a monosaccharide linkage-type analysis (GC-MS profile) of *C. difficile* polysaccharide PS-II, which shows the sugar linkage-types present in PS-II.

The term "*Clostridium difficile*" as used herein includes all strains of *Clostridium difficile*, including for example, ribotype 027 (also known as NAP1 and BI), ribotype W (also known as NAP2), MOH 900 and MOH 718.

The term "isolated" as used herein refers to *Clostridium difficile* cell surface polysaccharides substantially free of bacterial cell material or extraction solvent when produced from growing bacterial strains of *Clostridium difficile*.

As used herein the term "*Clostridium difficile* cell surface polysaccharides" includes those isolated from bacterial strains of *Clostridium difficile*, and also includes polysaccharides produced synthetically to have the same structure and/or composition of the *Clostridium difficile* cell surface polysaccharides disclosed herein. "Produced synthetically" includes for example, cell surface polysaccharides produced from techniques such as recombinant DNA technology, genetic knockout mice and/or chemical synthesis.

The term "covalent chemical structure" as used herein means the chemical formula for a compound where all groups are linked via covalent bonds.

As used herein the term "fragment thereof" means any portion of the cell surface polysaccharides disclosed herein that retains immunogenic activity against *Clostridium difficile*. The fragment may contain one or more if the monosaccharides (sugars) or sugar phosphates that are within the covalent chemical structures of the polysaccharides. Whether or not the fragment retains immunogenic activity may be determined using techniques known in the art.

As used herein the term "immunogenic" means the ability to elicit an immune response.

As used herein the term "vaccine" refers to a composition that prevents *Clostridium difficile* infection, treats *Clostridium difficile* infection and/or reduces shedding of *Clostridium difficile*.

The term "therapeutically effective amount", "effective amount" or "sufficient amount" means a quantity sufficient to, when administered to the subject, including a mammal, for example a human, achieve a desired result, for example an amount effect to elicit an immune response in a subject. Effective amounts of therapeutic may vary according to factors such as the disease state, age, sex, weight of the animal. Dosage or treatment regime may be adjusted to provide the optimum therapeutic response.

Moreover, a "treatment" regime of a subject with a therapeutically effective amount may consist of a single administration, or alternatively comprise a series of applications. The length of the treatment period depends on a variety of factors, such as the severity of the disease, the age of the patient, the concentration and the activity of the polysaccharides, or a combination thereof. It will also be appreciated that the effective dosage of the compound used for the treatment or prevention may increase or decrease over the course of a particular treatment or prevention regime. Changes in dosage may result and become apparent by standard diagnostic assays known in the art. The compounds of the present disclosure may be administered before, during or after exposure to the bacteria.

The expression "biologically compatible form in vivo" as used herein means a form of the substance to be administered in which any toxic effects are outweighed by the therapeutic effects.

The term "eliciting an immune response" or "inducing an immune response" as used herein means initiating, triggering, causing, enhancing, improving or augmenting any response of the immune system, for example, of either a humoral or cell-mediated nature. The initiation or enhancement of an immune response can be assessed using assays known to those skilled in the art including, but not limited to, antibody assays (for example ELISA assays), antigen specific cytotoxicity assays and the production of cytokines (for example ELISPOT assays).

The term "subject" as used herein refers to any member of the animal kingdom, preferably a mammal. In one embodiment, the mammal is a dog, a cat, a hamster, a mouse, a rat, a pig, a horse, cattle or a human being. In another embodiment, the mammal is a pig, a horse, cattle or a human being.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

For example, the phrase "treating or preventing *Clostridium difficile* infection" includes inhibiting *Clostridium difficile* infection, preventing *Clostridium difficile* infection, decreasing the severity of *Clostridium difficile* infection, inhibiting *Clostridium difficile* colonization, reducing shedding of *Clostridium difficile*, preventing *Clostridium difficile* colonization or improving signs and symptoms related to *Clostridium difficile* infection and the phrase "treating or preventing *Clostridium difficile*-associated diarrhea" includes inhibiting *Clostridium difficile*-associated diarrhea, preventing *Clostridium difficile*-associated diarrhea, decreasing the severity of *Clostridium difficile*-associated diarrhea or improving signs and symptoms related to having *Clostridium difficile*-associated diarrhea. The present application also include the treatment or prevention of any disease that is associated with a *Clostridium difficile* infection.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

II. Compounds and Compositions of the Application

As mentioned above, the present application describes the isolation and identification of the covalent chemical structure of *Clostridium difficile* cell surface polysaccharides. These novel polysaccharides are exposed on the cell surface of *Clostridium difficile* and can be used in immunogenic compositions, carbohydrate-based vaccine preparations and/or as diagnostic markers.

Accordingly, the present application includes isolated immunogenic *Clostridium difficile* cell surface polysaccharides. The present application also includes a *Clostridium difficile* cell surface polysaccharide mixture comprising one or more *Clostridium difficile* cell surface polysaccharides.

The present application also includes an immunogenic composition comprising one or more *Clostridium difficile* cell surface polysaccharides.

The present application further includes a vaccine composition comprising one or more *Clostridium difficile* cell surface polysaccharides.

The present application describes the isolation and characterization of three distinct cell surface *Clostridium difficile* cell surface polysaccharides. These are designated PS-I, PS-II and PS-III in the present application.

Using chemical analysis and analytical techniques, such as gas chromatography (GC), nuclear magnetic resonance (NMR) and mass spectrometry (MS), it has been determined that PS-I is a polymer of repeating pentasaccharide units linked through phosphodiester bonds and PS-II is a polymer of repeating hexasaccharide units also linked through phosphodiester bonds. In some preparations, polysaccharide PS-II may contain an additional glucose. Specifically, PS-I was found to be a branched pentaglycosyl phosophate repeating unit composed of glycosyl phosphate, rhamnose and glucose, PS-II was found to be a branched hexaglycosyl phosphate repeating unit composed of glucose, mannose, N-acetyl-galactosamine and glycosyl phosphate, and PS-III was determined to be composed of glycerol, alditol phosphate, glucose and N-acetyl-glucosamine.

In an embodiment, the cell surface polysaccharides are obtained by isolation from strains of *Clostridium difficile* bacteria, for example by growing *Clostridium difficile* bacteria in suitable medium, separating bacterial cells from the medium, extracting cell surface polysaccharides by mild acid treatment under conditions to cleave the polysaccharides from the cell surface material, and purifying the extracted cell surface polysaccharides. In a further embodiment the mild acid is 0.1% to 5%, suitably 2% acetic acid. In a further embodiment the cell surface polysaccharides are purified or separated by centrifugation, size exclusion chromatography and/or anion exchange chromatography.

In one embodiment, the cell surface polysaccharides comprise repeating pentasaccharide units of the formula I:

(I)

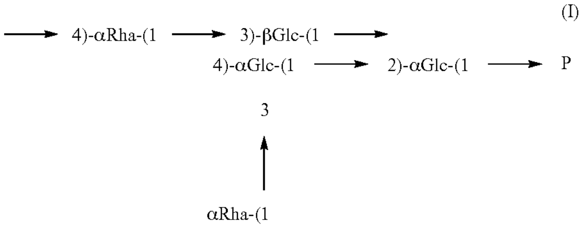

wherein Rha is rhamnose, P is glycosyl phosphate and Glc is glucose or an immunogenic fragment thereof.

In another embodiment, the cell surface polysaccharides are compounds of the formula PS-I:

(PS-I)

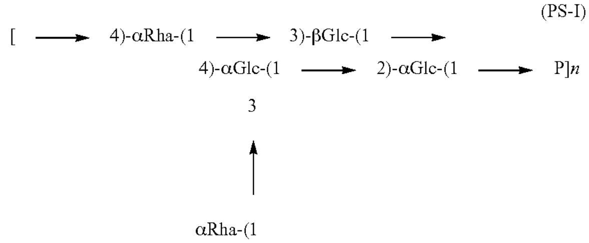

wherein n is an integer from 1 to 1000, Rha is rhamnose, P is glycosyl phosphate and Glc is glucose or an immunogenic fragment thereof.

In one embodiment, the monosaccharides in PS-I, rhamnose and glucose, are present in the pyranose confirmation.

In another embodiment, n in PS-I is an integer from 1 to 100, 2 to 100, 10 to 100, or 25 to 100.

In another embodiment, the cell surface polysaccharides (PS-I) comprise glycosyl phosphate, rhamnose and glucose.

In another embodiment, the cell surface polysaccharides comprise repeating hexasaccharide units of the formula II:

(II)

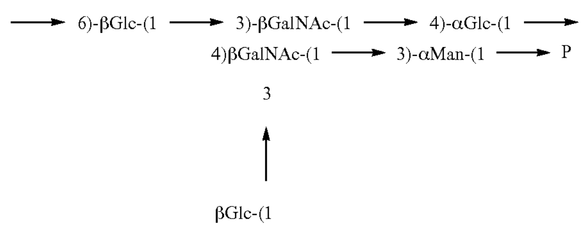

wherein Glc is glucose, GalNAc is N-acetyl-galactosamine, P is glycosyl phosphate and Man is mannose or an immunogenic fragment thereof.

In another embodiment, the cell surface polysaccharides are compounds of the formula PS-II:

(PS-II)

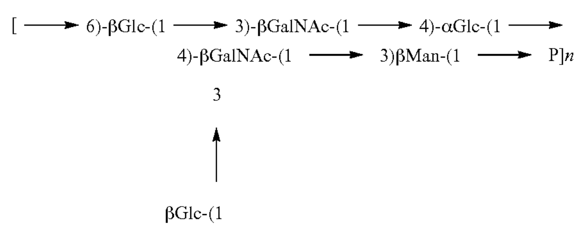

wherein, n is an integer from 1 to 1000, Glc is glucose, GalNAc is N-acetyl-galactosamine, P is glycosyl phosphate and Man is mannose or an immunogenic fragment thereof.

In one embodiment, the monosaccharides in PS-II, glucose, N-acetyl-galactosamine and mannose, are present in the pyranose conformation.

In another embodiment, n in PS-II is an integer from 1 to 100, 2 to 100, 10 to 100, or 25 to 100.

In another embodiment, the cell surface polysaccharides (PS-II) comprise glucose, mannose, N-acetyl-galactosamine and glycosyl phosphate within their covalent chemical structure.

In another embodiment, the covalent chemical structure of cell surface polysaccharides (PS-III) comprises glycerol, alditol phosphate, glucose and N-acetyl-glucosamine.

In another embodiment, the covalent chemical structure of cell surface polysaccharides (PS-III) consists of glycerol, alditol phosphate, glucose and N-acetyl-glucosamine.

Another aspect of the present application is a cell surface polysaccharide mixture comprising at least two of: a) cell surface polysaccharides PS-I disclosed herein; or b) cell surface polysaccharides PS-II disclosed herein; or c) cell surface polysaccharides PS-III disclosed herein; where the cell surface polysaccharide mixture comprises at least two of the cell surface polysaccharides in a), b) or c) in any combination.

In one embodiment, the cell surface polysaccharide mixture comprises: a) cell surface polysaccharides PS-I disclosed herein and b) cell surface polysaccharides PS-II disclosed herein.

In another embodiment, the present application discloses an immunogenic composition comprising one or more *Clostridium difficile* cell surface polysaccharides and a pharmaceutically acceptable excipient, carrier, buffer, stabilizer, or mixtures thereof.

In one embodiment, the immunogenic composition comprises cell surface polysaccharides comprising repeating pentasaccharide units of the formula I:

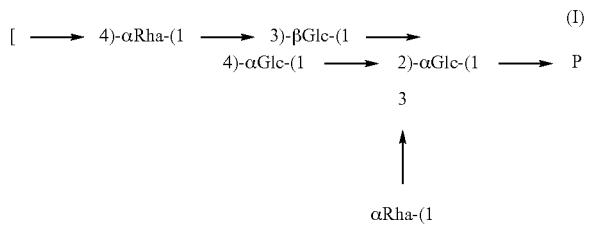

wherein Rha is rhamnose, P is glycosyl phosphate and Glc is glucose or an immunogenic fragment thereof.

In another embodiment, the immunogenic composition comprises cell surface polysaccharides of the formula PS-I:

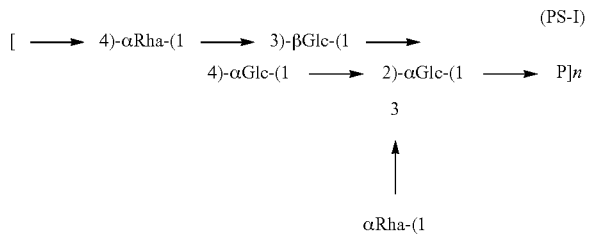

wherein n is an integer from 1 to 1000, Rha is rhamnose, P is glycosyl phosphate and Glc is glucose or an immunogenic fragment thereof.

In one embodiment, the monosaccharides in PS-I, rhamnose and glucose, are present in the pyranose confirmation.

In another embodiment, n in PS-I is an integer from 1 to 100, 2 to 100, 10 to 100, or 25 to 100.

In another embodiment, the immunogenic composition comprises cell surface polysaccharides (PS-I) comprising glycosyl phosphate, rhamnose and glucose within their covalent chemical structure.

In another embodiment, the immunogenic composition comprises cell surface polysaccharides comprising repeating hexasaccharide units of the formula (II):

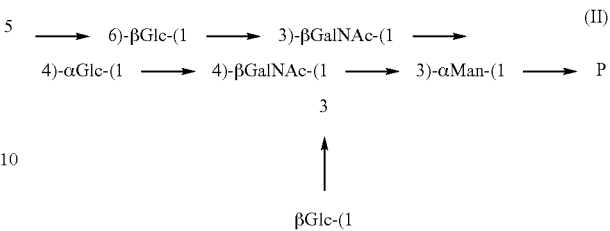

wherein Glc is glucose, GalNAc is N-acetyl-galactosamine, P is glycosyl phosphate and Man is mannose or an immunogenic fragment thereof.

In another embodiment, the immunogenic composition comprises cell surface polysaccharides of the formula PS-II:

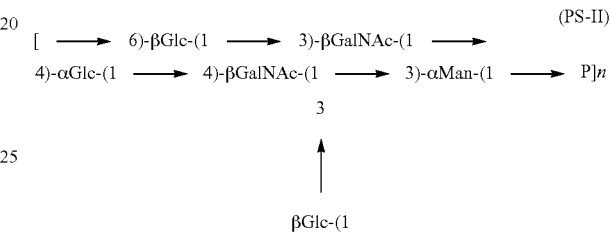

wherein, n is an integer from 1 to 1000, Glc is glucose, GalNAc is N-acetyl-galactosamine, P is glycosyl phosphate and Man is mannose or an immunogenic fragment thereof.

In one embodiment, the monosaccharides in PS-II, glucose, N-acetyl-galactosamine, and mannose, are present in the pyranose conformation.

In another embodiment, n in PS-II is an integer from 1 to 100, 2 to 100, 10 to 100, or 25 to 100.

In another embodiment, the immunogenic composition comprises cell surface polysaccharides (PS-II) comprising glucose, mannose, N-acetyl-galactosamine and glycosyl phosphate within their covalent chemical structure.

In another embodiment, the immunogenic composition comprises a cell surface polysaccharides (PS-III) comprising glycerol, alditol phosphate, glucose and N-acetyl-glucosamine within their covalent chemical structure.

In another embodiment, the immunogenic composition comprises cell surface polysaccharides (PS-III) consisting of glycerol, alditol phosphate, glucose and N-acetyl-glucosamine within their covalent chemical structure.

Another aspect of the present application is an immunogenic composition comprising a mixture of at least two of: a) the immunogenic composition comprising cell surface polysaccharides PS-I disclosed herein; or b) the immunogenic composition comprising cell surface polysaccharides PS-II disclosed herein; or c) the immunogenic composition comprising cell surface polysaccharides PS-III disclosed herein; where the immunogenic composition mixture comprises at least two of the immunogenic compositions in a), b) or c) in any combination.

Another aspect of the present application is an immunogenic composition comprising a cell surface polysaccharide mixture comprising at least two of: a) the cell surface polysaccharides PS-I disclosed herein; or b) the cell surface polysaccharides PS-II disclosed herein; or c) the cell surface polysaccharides PS-III disclosed herein; where the immunogenic composition comprises at least two of the cell surface polysaccharides in a), b) or c) in any combination.

In one embodiment of the present application, an immunogenic composition comprises a mixture of cell surface polysaccharides comprising: a) cell surface polysaccharides PS-I disclosed herein and b) cell surface polysaccharides PS-II disclosed herein.

In another embodiment, the present application discloses a vaccine composition comprising one or more *Clostridium difficile* cell surface polysaccharides and a pharmaceutically acceptable excipient, carrier, buffer, stabilizer, or mixtures thereof.

In one embodiment, the vaccine composition comprises cell surface polysaccharides comprising repeating pentasaccharide units of the formula I:

$$[\longrightarrow 4)\text{-}\alpha\text{Rha-}(1 \longrightarrow 3)\text{-}\beta\text{Glc-}(1 \longrightarrow \atop \begin{array}{c} 4)\text{-}\alpha\text{Glc-}(1 \longrightarrow 2)\text{-}\alpha\text{Glc-}(1 \longrightarrow P \\ 3 \\ \uparrow \\ \alpha\text{Rha-}(1 \end{array}] \quad (I)$$

wherein Rha is rhamnose, P is glycosyl phosphate and Glc is glucose or an immunogenic fragment thereof.

In one embodiment, the vaccine composition comprises cell surface polysaccharides of the formula PS-I:

$$[\longrightarrow 4)\text{-}\alpha\text{Rha-}(1 \longrightarrow 3)\text{-}\beta\text{Glc-}(1 \longrightarrow \atop \begin{array}{c} 4)\text{-}\alpha\text{Glc-}(1 \longrightarrow 2)\text{-}\alpha\text{Glc-}(1 \longrightarrow P]n \\ 3 \\ \uparrow \\ \alpha\text{Rha-}(1 \end{array}] \quad (\text{PS-I})$$

wherein n is an integer from 1 to 1000, Rha is rhamnose, P is glycosyl phosphate and Glc is glucose or an immunogenic fragment thereof.

In one embodiment, the monosaccharides in PS-I, rhamnose and glucose, are present in the pyranose confirmation.

In another embodiment, n in PS-I is an integer from 1 to 100, 2 to 100, 10 to 100, or 25 to 100.

In another embodiment, the vaccine composition comprises a cell surface polysaccharides (PS-I) comprising glycosyl phosphate, rhamnose and glucose within their covalent chemical structure.

In another embodiment, the vaccine composition comprises cell surface polysaccharides comprising repeating hexasaccharide units of the formula II:

$$[\longrightarrow 6)\text{-}\beta\text{Glc-}(1 \longrightarrow 3)\text{-}\beta\text{GalNAc-}(1 \longrightarrow 4)\text{-}\alpha\text{Glc-}(1 \longrightarrow \atop \begin{array}{c} 4)\text{-}\beta\text{GalNAc-}(1 \longrightarrow 3)\text{-}\alpha\text{Man-}(1 \longrightarrow P \\ 3 \\ \uparrow \\ \beta\text{Glc-}(1 \end{array}] \quad (II)$$

wherein Glc is glucose, GalNAc is N-acetyl-galactosamine, P is glycosyl phosphate and Man is mannose or an immunogenic fragment thereof.

In another embodiment, the vaccine composition comprises cell surface polysaccharides of the formula PS-II:

$$[\longrightarrow 6)\text{-}\beta\text{Glc-}(1 \longrightarrow 3)\text{-}\beta\text{GalNAc-}(1 \longrightarrow \atop \begin{array}{c} 4)\text{-}\alpha\text{Glc-}(1 \longrightarrow 4)\text{-}\beta\text{GalNAc-}(1 \longrightarrow 3)\text{-}\alpha\text{Man-}(1 \longrightarrow P]n \\ 3 \\ \uparrow \\ \beta\text{Glc-}(1 \end{array}] \quad (\text{PS-II})$$

wherein, n is an integer from 1 to 1000, Glc is glucose, GalNAc is N-acetyl-galactosamine, P is glycosyl phosphate and Man is mannose or an immunogenic fragment thereof.

In one embodiment, the monosaccharides in PS-II, glucose, N-acetyl-galactosamine and mannose, are present in the pyranose conformation.

In another embodiment, n in PS-II is an integer from 1 to 100, 2 to 100, 10 to 100, or 25 to 100.

In another embodiment, the vaccine composition comprises cell surface polysaccharides (PS-II) comprising glucose, mannose, N-acetyl-galactosamine and glycosyl phosphate within their covalent chemical structure.

In another embodiment, the vaccine composition comprises cell surface polysaccharides (PS-III) comprising glycerol, alditol phosphate, glucose and N-acetyl-glucosamine within their covalent chemical structure.

In another embodiment, the vaccine composition comprises cell surface polysaccharides (PS-III) consisting of glycerol, alditol phosphate, glucose and N-acetyl-glucosamine within their covalent chemical structure.

Another aspect of the present application is a vaccine composition comprising a mixture of at least two of: a) the vaccine composition comprising cell surface polysaccharides PS-I disclosed herein; or b) the vaccine composition comprising cell surface polysaccharides PS-II disclosed herein; or c) the vaccine composition comprising cell surface polysaccharides PS-III disclosed herein; where the vaccine composition mixture comprises at least two of the vaccine compositions in a), b) or c) in any combination.

Another aspect of the present application is a vaccine composition comprising a cell surface polysaccharide mixture comprising at least two of: a) the cell surface polysaccharides PS-I disclosed herein; or b) the cell surface polysaccharides PS-II disclosed herein; or c) the cell surface polysaccharides PS-III disclosed herein; where the vaccine composition comprises at least two of the cell surface polysaccharides in a), b) or c) in any combination.

In one embodiment of the present application, a vaccine composition comprises a mixture of cell surface polysaccharides comprising: a) cell surface polysaccharides PS-I disclosed herein and b) cell surface polysaccharides PS-II disclosed herein.

Glycoconjugate vaccines are known to enhance the immunogenic properties of carbohydrates. Hence, by coupling *Clostridium difficile* cell surface polysaccharides to a carrier molecule, it is possible to maximize the immunogenic response of the carbohydrate-based vaccine.

Accordingly, in another embodiment of the present application there is included one or more of the *Clostridium difficile* cell surface polysaccharides disclosed herein conjugated to a carrier molecule.

In another embodiment, the cell surface polysaccharides comprising repeating pentasaccharide units of the formula I are conjugated to a carrier molecule. In another embodiment, the cell surface polysaccharides PS-I are conjugated to a carrier molecule. In another embodiment, the cell surface polysaccharides comprising repeating hexasaccharide units of the formula II are conjugated to a carrier molecule. In another embodiment, the cell surface polysaccharides PS-II are conjugated to a carrier molecule. In another embodiment, the cell surface polysaccharides PS-III are conjugated to a carrier molecule.

Another embodiment of the present application is an immunogenic composition comprising one or more of the *Clostridium difficile* cell surface polysaccharides disclosed herein conjugated to a carrier molecule.

A further embodiment of the present application is a vaccine composition comprising one or more of the *Clostridium difficile* cell surface polysaccharides disclosed herein conjugated to a carrier molecule.

In one embodiment, the carrier molecule is a protein. In another embodiment the carrier molecule is bovine serum albumin (BSA). In another embodiment, the carrier molecule is cross reactive material, for example, $CRM_{197}$. $CRM_{197}$ is a nontoxic version of a Diphtheria toxin that has been successfully used in pneumococcal conjugate vaccines (Anderson, P. W., 1983, Infect. Immun. 39:233-238). In another embodiment, the carrier molecule is MIEP (major immunoenhancing protein). MIEP may be derived from the outer membrane complex of *Neisseria* meningitis type B and other meningococcal group B (Merck). In another embodiment, the carrier molecule is Diphtheria toxoid. In a further embodiment, the carrier molecule is Tetanus toxoid. In another embodiment, the carrier molecule is a protein derived from *Bordetella*.

The carrier molecule may be attached to the cell surface polysaccharide using known methods. For example, via an ester or amide linkage between available hydroxy or carboxy groups on the saccharides and carboxyl or amine groups on the protein.

Other carrier molecules and methods of their attachment have been previously reported (see for example U.S. Pat. No. 4,673,574, the contents of which are incorporated herein by reference).

Immunogenicity can be significantly improved if the immunizing agent (i.e. the *Clostridium difficile* cell surface polysaccharide or the immunogenic compositions comprising the *Clostridium difficile* cell surface polysaccharides or the vaccine compositions comprising *Clostridium difficile* cell surface polysaccharides disclosed in the present application) is regardless of administration format, co-immunized with an immunostimulatory component, such as an adjuvant. Adjuvants enhance the immunogenicity of an immunogen but are not necessarily immunogenic in of themselves. Adjuvants may act by retaining the immunogen locally near the site of administration to produce a depot effect facilitating a slow, sustained release of immunogen to cells of the immune system. Adjuvants can also attract cells of the immune system to an immunogen depot and stimulate such cells to elicit immune response. As such, embodiments of this present application encompass compositions including for example immunogenic, vaccine or pharmaceutical compositions further comprising adjuvants.

Another aspect of the present application is an immunogenic composition comprising one or more of the *Clostridium difficile* cell surface polysaccharides disclosed herein and an immunostimulatory component, such as an adjuvant.

Another aspect of the present application is a vaccine composition comprising one or more of the *Clostridium difficile* cell surface polysaccharides disclosed herein and an immunostimulatory component, such as an adjuvant.

Adjuvants have been used for many years to improve the host immune responses to, for example, vaccines. Intrinsic adjuvants (such as lipopolysaccharides) normally are the components of killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to Diphtheria and Tetanus toxoids is well established.

A wide range of extrinsic adjuvants can provoke potent immune responses to immunogens. These include saponins complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

In one aspect of the present application, adjuvants useful in any of the embodiments described herein are as follows. Adjuvants for parenteral immunization include aluminum compounds (such as aluminum hydroxide, aluminum phosphate, and aluminum hydroxy phosphate). The antigen can be precipitated with, or adsorbed onto, the aluminum compound according to standard protocols. Other adjuvants such as RIBI (ImmunoChem, Hamilton, Mont.) can also be used in parenteral administration.

Adjuvants for mucosal immunization include bacterial toxins (e.g., the cholera toxin (CT), the *E. coli* heat-labile toxin (LT), the *Clostridium difficile* toxin A and the pertussis toxin (PT), or combinations, subunits, toxoids, or mutants thereof). For example, a purified preparation of native cholera toxin subunit B (CTB) can be of use. Fragments, homologs, derivatives, and fusion to any of these toxins are also suitable, provided that they retain adjuvant activity. Preferably, a mutant having reduced toxicity is used. Suitable mutants have been described (e.g., in WO 95/17211 (Arg-7-Lys CT mutant), WO 96/6627 (Arg-192-Gly LT mutant), and WO 95/34323 (Arg-9-Lys and Glu-129-Gly PT mutant)). Additional LT mutants that can be used in the methods and compositions disclosed herein include, for example Ser-63-Lys, Ala-69-Gly, Glu-110-Asp, and Glu-112-Asp mutants. Other adjuvants (such as a bacterial monophosphoryl lipid A (MPLA) of various sources (e.g., *E. coli, Salmonella minnesota, Salmonella typhimurium,* or *Shigella flexneri,* saponins, or polylactide glycolide (PLGA) microspheres) can also be used in mucosal administration.

Adjuvants useful for both mucosal and parenteral immunization include polyphosphazene (for example, WO 95/2415), DC-chol (3 b-(N—(N',N'-dimethyl aminomethane)-carbamoyl)cholesterol (for example, U.S. Pat. No. 5,283,185 and WO 96/14831) and QS-21 (for example, WO 88/9336).

A subject may be immunized with a composition including for example an immunogenic, vaccine or pharmaceutical composition comprising the *Clostridium difficile* cell surface polysaccharides disclosed in the present application by any conventional route as is known to one skilled in the art. This may include, for example, immunization via a mucosal (e.g., ocular, intranasal, oral, gastric, pulmonary, intestinal, rectal, vaginal, or urinary tract) surface, via the parenteral (e.g., subcutaneous, intradermal, intramuscular, intravenous, or intraperitoneal) route or intranodally. Preferred routes depend upon the choice of the immunogen as will be apparent to one skilled in the art. The administration can be achieved in a single dose or repeated at intervals. The appropriate dosage depends on various parameters understood by skilled artisans such as the immunogen itself (i.e. peptide vs. nucleic acid (and more specifically type thereof), the route of administration and the condition of the animal to be vaccinated (weight, age and the like).

The *Clostridium difficile* cell surface polysaccharides or immunogenic compositions or vaccine compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, 20th ed., Mack Publishing Company, Easton, Pa., USA, 2000). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween™), alcohols, polyols, glycerin and vegetable oils, for example. Extemporaneous injection solutions and suspensions may be prepared from sterile powders, granules, tablets, or concentrated solutions or suspensions. The pharmaceutical composition may be supplied, for example but not by way of limitation, as a lyophilized powder which is reconstituted with sterile water or saline prior to administration to the patient.

Compositions including for example immunogenic, vaccine or pharmaceutical compositions of the present application may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy) propyl)N,N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The compositions disclosed in the present application can be administered for example, by parenteral, intravenous, subcutaneous, intramuscular, intracranial, intraorbital, ophthalmic, intraventricular, intracapsular, intraspinal, intracisternal, intraperitoneal, intranasal, aerosol or oral administration.

Accordingly, another embodiment of the present application is a pharmaceutical composition comprising an effective amount of a *Clostridium difficile* cell surface polysaccharide disclosed herein in admixture with a suitable excipient, diluent, carrier, buffer or stabilizer.

In a suitable embodiment, the pharmaceutical compositions are suitable for administration to subjects in a biologically compatible form in vivo.

Another aspect of the present application is a kit comprising the cell surface polysaccharides disclosed herein or the cell surface polysaccharide mixture disclosed herein or the immunogenic compositions disclosed herein or the vaccine compositions disclosed herein or the pharmaceutical compositions disclosed herein, and instructions for use thereof.

The kit can also include ancillary agents. For example, the kit can include an instrument for injecting the immunogenic composition of the present application into a subject, such as a syringe; a vessel for storing or transporting the immunogenic composition; and/or pharmaceutically acceptable excipients, carriers, buffers or stabilizers.

III. Methods and Uses of the Application

Another aspect of the present application is a method of inducing an immune response against *Clostridium difficile* in a subject by administering to the subject an effective amount of one or more of the *Clostridium difficile* cell surface polysaccharides disclosed herein.

A further aspect of the present application is a method of treating or preventing *Clostridium difficile* infection in a subject by administering to the subject an effect amount of one or more of the *Clostridium difficile* cell surface polysaccharides disclosed herein.

An additional aspect of the present application is a method of treating or preventing *Clostridium difficile*-associated diarrhea in a subject by administering to the subject an effective amount of one or more of the *Clostridium difficile* cell surface polysaccharides disclosed herein.

The present application also discloses uses of one or more of the *Clostridium difficile* cell surface polysaccharides disclosed herein to induce an immune response against *Clostridium difficile* in a subject, to treat or prevent *Clostridium difficile* infection in a subject, and to treat or prevent *Clostridium difficile*-associated diarrhea in a subject.

Other aspects of the present application include uses of one or more of the *Clostridium difficile* cell surface polysaccharides disclosed herein for the manufacture of a medicament to induce an immune response against *Clostridium difficile* in a subject, to treat or prevent *Clostridium difficile* infection, and to treat or prevent *Clostridium difficile*-associated diarrhea.

Another aspect of the present application is a method of inducing an immune response against *Clostridium difficile* in a subject by administering to the subject an effective amount of the immunogenic compositions disclosed herein where the immunogenic composition comprises one or more of the *Clostridium difficile* cell surface polysaccharides disclosed herein.

A further aspect of the present application is a method of treating or preventing *Clostridium difficile* infection in a subject by administering to the subject an effective amount of the immunogenic compositions disclosed herein where the immunogenic composition comprises one or more of the *Clostridium difficile* cell surface polysaccharides disclosed herein.

An additional aspect of the present application is a method of treating or preventing *Clostridium difficile*-associated diarrhea in a subject by administering to the subject an effective amount of the immunogenic compositions disclosed herein where the immunogenic composition comprises one or more of the *Clostridium difficile* cell surface polysaccharides disclosed herein.

The present application also discloses uses of the immunogenic compositions disclosed herein where the immunogenic composition comprises one or more of the *Clostridium difficile* cell surface polysaccharides disclosed herein to induce an immune response against *Clostridium difficile* in a subject, to treat or prevent *Clostridium difficile* infection in a subject, and to treat or prevent *Clostridium difficile*-associated diarrhea in a subject.

Other aspects of the present application include uses of the immunogenic compositions disclosed herein where the immunogenic composition comprises one or more of the *Clostridium difficile* cell surface polysaccharides disclosed herein for the manufacture of a medicament to induce an immune response in a subject against *Clostridium difficile*, to treat or prevent *Clostridium difficile* infection, and to treat or prevent *Clostridium difficile*-associated diarrhea.

Another aspect of the present application is a method of inducing an immune response against *Clostridium difficile* in a subject by administering to the subject an effective amount of the vaccine compositions disclosed herein where the vaccine composition comprises one or more of the *Clostridium difficile* cell surface polysaccharides disclosed herein.

A further aspect of the present application is a method of treating or preventing *Clostridium difficile* infection in a subject by administering to the subject an effective amount of the vaccine compositions disclosed herein where the vaccine composition comprises one or more of the *Clostridium difficile* cell surface polysaccharides disclosed herein.

An additional aspect of the present application is a method of treating or preventing *Clostridium difficile*-associated diarrhea in a subject by administering to the subject an effective amount of the vaccine compositions disclosed herein where the vaccine composition comprises one or more of the *Clostridium difficile* cell surface polysaccharides disclosed herein.

The present application also discloses uses of the vaccine compositions disclosed herein where the vaccine composition comprises one or more of the *Clostridium difficile* cell surface polysaccharides disclosed herein to induce an immune response against *Clostridium difficile* in a subject, to treat or prevent *Clostridium difficile* infection in a subject, and to treat or prevent *Clostridium difficile*-associated diarrhea in a subject.

Other aspects of the present application include uses of the vaccine compositions disclosed herein where the vaccine composition comprises one or more of the *Clostridium difficile* cell surface polysaccharides disclosed herein for the manufacture of a medicament to induce an immune response against *Clostridium difficile* in a subject, to treat or prevent *Clostridium difficile* infection, and to treat or prevent *Clostridium difficile*-associated diarrhea.

The methods and uses of the present application are applicable to subjects including for example, pigs, horses, cattle or human beings.

The present application also includes methods and uses of the *Clostridium difficile* cell surface polysaccharides as diagnostic markers for a *Clostridium difficile* infection. For example, since *Clostridium difficile* ribotype 027 uniquely possess PS-1, the presence of this polysaccharide in its cellular material can indicate the presence this ribotype in a sample. The sample may be from a human or animal subject or from food or water, or other substance, suspected of infection with *Clostridium difficile*.

Accordingly the present application includes of method of detecting *Clostridium difficile* in a test sample comprising assaying the sample for the presence of one or more of the isolated cell surface polysaccharides disclosed herein. The application also includes the use of one or more of the isolated cell surface polysaccharides disclosed herein to detect *Clostridium difficile* in a test sample.

The presence of one of more of the isolated cell surface polysaccharides disclosed herein may be assayed, for example, by isolating the polysaccharides from the sample and performing chemical analyses to determined the identity of the saccharides that are present in the polysaccharide. Such chemical analyses can include one or more of (i) GLC-MS of the corresponding alditol acetates, MS and NMR spectroscopy.

The above disclosure generally describes the present invention. A more complete understanding can be obtained by reference to the following specific examples. These examples are described solely for the purpose of illustration and are not intended to limit the scope of the invention. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present invention:

IV. Examples

Three *C. difficile* strains were chosen for investigation. One particular strain, designate ribotype 027 or North American pulsotype 1 (NAP1) has emerged as an important cause of sporadic and epidemic disease internationally. Serious outbreaks with high morbidity, high mortality, poor response to treatment and high relapse rates have been reported. This strain produces three main toxins: toxin A, toxin B and CDT (binary toxin). The other strains under investigation are *C. difficile* MOH 900, which expresses only two of the three toxins (toxin A and B) and has been found to be more prevalent in Canada, and *C. difficile* MOH 718, an uncommon toxin variant that possesses genes encoding for toxin B, but not toxins A or CDT.

*C. difficile* is a spore-forming bacterium that resists phagocytosis by cell surface polysaccharides. In view of vaccine development, targeting this exposed carbohydrate chain on the cell surface may prove to be beneficial. Hence, in an attempt to develop a glycoconjugate vaccine, the present application describes the isolation and characterization of *C. difficile* cell-surface polysaccharides for subsequent use in for example, carbohydrate-based vaccine preparation.

Materials and Methods:

Bacterial Growth and Isolation of Polysaccharides:

A ribotype 027 isolate that was obtained from a person with *C. difficile* associated disease was used for the study. In all cases, cells were grown in CDMN broth (*Clostridium difficile* Moxalactam Norfloxacin) at 37° C. for 24 h in anaerobic chamber, then washed with phosphate buffered saline, separated by centrifugation and freeze-dried. The cell surface polysaccharides were isolated from the bacterial cell surface by a 2% acetic acid treatment to selectively cleave polysaccharides from peptidoglycan. Polysaccharides PS-I and PS-II were obtained from the aqueous layer and polysaccharide PS-III was obtained from the pellet material. Subsequent purification steps through size exclusion chromatography and anion exchange chromatography were also performed.

Analytical Procedures:

The determination of sugar components in the form of alditol acetates was carried out using GLC-MS (Sawardeker, J. S.; Sloneker, J. H.; Jeanes, A. *Anal. Chem.* 1965, 37(12), 1602-1604). Samples were hydrolyzed with trifluoroacetic acid and the hydrolysate was then reduced with sodium borodeuteride and acetylated with acetic anhydride. The acetylated monosaccharide derivatives were then analyzed by GLC-MS. Linkage analysis was carried out by the NaOH-DMSO-methyl iodide procedure (Hakomori, S.; *J. Biochem (Tokyo).* 1964, 55, 205-208; Lindberg, B.; *Methods Enzymol.* 1972, 28, 178-195) and analyzed by GLC-MS as above. Dephosphorylation of the polysaccharides was achieved through 48% HF treatment (Kenne, L.; Lindberg, S.; Rahman, M.; Mosihuzzaman, M. *Carb Res.* 1993, 247, 181-189).

Mass Spectrometry:

Matrix assisted laser desorption ionization-time of flight-mass spectrometry (MALD)-TOF-MS) was performed using sinapinic acid as the matrix.

NMR Spectroscopy:

The samples were exchanged with deuterium oxide, lyophilized, and dissolved in 600 μL of $D_2O$, Spectra were recorded at 298 K using standard pulse sequences for 2D experiments.

Immunogenicity of *Clostridium difficile* CSP Inoculations in Pigs:

Ten sows from a local swine operation were used. All sows included in the study were healthy with no signs of systemic disease, no history of previous adverse reactions to vaccines or other intramuscular injections, and no history of diarrhea within the previous 30 days. The pigs were divided randomly into 2 groups (n=5, each). Sows were enrolled when they were approximately 30 days from the planned farrowing date. A mixture of *C. difficile* cell surface polysaccharides PS-I and PS-II (400 ug/inoculation), dissolved in saline without adjuvant, was administered intramuscularly to all sows in Group 1. Sows in group 2 were injected with saline only, as controls. All sows were inoculated once at day 1 (first inoculation) and again at day 8 (second inoculation). The site of inoculation was recorded. On day 1, whole blood (10 ml) was collected from the infraorbital sinus. Sows were monitored hourly for the first 4 hours, then twice daily and the general appearance, attitude, appetite, urination, defecation, temperature, pulse, and respiratory rate were recorded. The injection site was evaluated for signs of inflammation (swelling, pain on palpation). Blood collection was repeated on day 8 and 15. Sera from day 1, 8 and 15 were analyzed by dot-blot analysis for Immunoglobulin M (IgM) specific to PS-I and PS-II. A whole cell preparation of *Campylobacter* coil was used as a positive control in the dot-blot test and BSA was used as the negative control. The dot-blot analysis was performed on a polyvinyldine difluoride (PVDF) membrane with HRP-conjugated IgM at 1:5000 dilution for PS-II and at 1:100 dilution for the mixture of PS-I/PS-II.

Results:

The aqueous polysaccharide preparation isolated from *C. difficile* ribotype 027 was subjected to size exclusion chromatography. The elution profile showed that the earlier eluting fractions were distinctly different from those eluting at a later time. A monosaccharide composition analysis performed on one of the earlier fractions (PS-I) revealed the presence of rhamnose and glucose residues, whereas the same analysis performed on later fractions (PS-II) showed mainly mannose and N-acetyl galactosamine residues. The aqueous polysaccharide preparation isolated from *C. difficile* MOH 900 and MOH 718 was found to only contain polysaccharide PS-II.

The major linkage-types determined to be present in PS-I were terminal Rha [Rha-(1→], 2-monosubstituted Glc [→2)-Glc-(1→], and 3-monosubstituted Glc [→3)-Glc-(1→], and 3,4-disubstituted Glc [→34)-Glc-(1→]. Traces of 4-monosubstituted Rha [→4)-Rha-(1→] were also observed. The analysis of the 2-(S)- and 2-(R)-butyl chiral glycosides revealed that Glc possessed the D and Rha the L enantiomeric configuration.

Monosaccharide composition analyses carried out on PS-II showed the presence of Glc, mannose (Man) and N-Acetyl-galactosamine (GalNAc), but also small amounts of Rha were also detected in PS-II. All units were observed to have the D enantiomeric configuration. Sugar linkage-type analysis performed on PS-II showed many variably linked monosaccharides units. The major linkage-types determined to be present in PS-II terminal Glc, 4-monosubstituted Glc, 3-monosubstituted Man, 3-substituted GalNAc, and 3,4-disubstituted GalNAc as main units. Co-eluting with the 4-monosubstituted Glc residue, trace amounts of m/z ions characteristic of 6-monosubstituted Glc (m/z 189) were also detected in PS-II. Additionally, small amounts of the linkage-types observed to be present in PS-I were also detected in the linkage-type analyses of PS-II. FIG. 1 shows the sugar linkage-types of polysaccharide PS-II that was obtained from *C. difficile* MOH 900.

Purification by anion exchange chromatography of the aqueous preparation of *C. difficile* ribotype 027 also gave rise to two distinct polysaccharides (PS-I and PS-II). $^1$H-NMR spectra of PS-I and PS-II (FIGS. 2A and 2B) showed five anomeric signals for PS-I (designated A through E) and six signals for PS-II (designated A through F). The polysaccharide PS-II isolated from *C. difficile* MOH 900 and MOH 718 cells gave identical $^1$H-NMR spectrum as PS-II of ribotype 027.

Additional 2-dimensional NMR experiments, both homonuclear (1H) and heteronuclear (1H, $^{13}$C, and $^{31}$P), were used to establish the sequence of PS-I (FIG. 3) and PS-II. 2D $^1$H-$^1$H COSY, TOCSY and $^1$H-$^{13}$C HSQC experiments allowed the assignment of most of the ring protons and carbons of each unit present in PS-I and PS-II. The determination of the sequence of monosaccharide residues was made possible by $^1$H-$^{13}$C HMBC and $^1$H-$^1$H NOESY (FIG. 3) experiments which allowed the assignment of the glycosyl linkages in PS-I. The 2D $^1$H-$^1$H NOESY (FIG. 3) performed on PS-I revealed inter-nOe connectivities (schematically shown below in FIG. 3) between H-1 ($\delta_H$ 5.23) of the terminal αRha (B) and H-3 ($\delta_H$ 4.01) of the branched 3,4-substituted αGlc (D) for [α-Rha-(1→3)-α-Glc-(1→], between H-1 ($\delta_H$ 5.17) of the 4-substituted αRha (C) and H-3 ($\delta_H$ 3.62) of the 3-substituted βGlc (E) for [→4)-αRha-(1→3)-βGlc-(1→], between H-1 ($\delta_H$ 5.13) of the branched 3,4-substituted αGlc (D) and H-2 ($\delta_H$ 3.68) of the 2-substituted βGlc (A) for [→3/4)-αGlc-(1→2)-αGlc-(1→], and between H-1 ($\delta_H$ 4.53) of the 3-substituted αGlc (E) and H-4 ($\delta_H$ 3.86) of the branched 3,4-substituted αGlc (D) for [→3)-βGlc-(1→4)-αGlc-(1→]. Other through-space interactions, many arising from intra-nOe connectivities, were also detected by the 2D $^1$H-$^1$H NOESY experiment, but, of particular note, the inter-nOe interaction between the anomeric protons of the branched 3,4-substituted αGlc (D; $\delta_H$ 5.13) and of the 2-substituted αGlc (A; $\delta_H$ 5.75) revealed the proximity of these two protons in the (1→2) glycosidic linkage between these two αGlc units [→3/4)-αGlc-(1→2)-αGlc-(1→]. The correlations detected in PS-I were:

H-1 (D)/C-2 (A) for [α-Glc-(1→2)-α-Glc]
H-1 (E)/C-4 (D) for [β-Glc-(1→4)-α-Glc]
H-1 (C)/C-3 (E) for [α-Rha-(1→3)-β-Glc]
H-1 (B)/C-3 (D) for [α-Rha-(1→3)-α-Glc]

Figure 4:
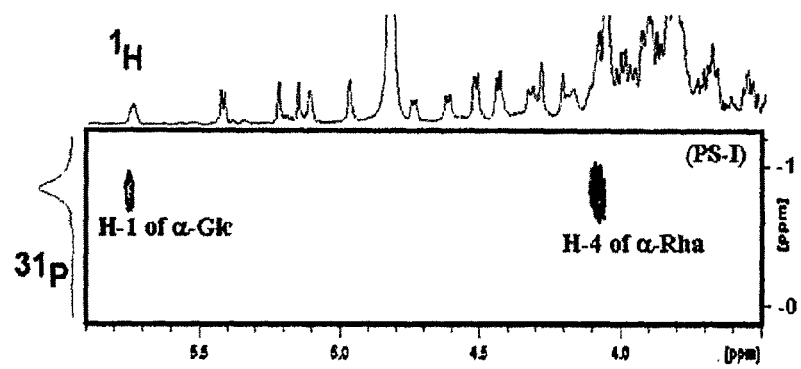
FIG. 4 shows (A) $^1$H-$^{31}$P-HMBC spectrum showing the connection of the glycosyl phosphate to the position number 1 of 2-linked Glc and to the position number 4 of the 4-linked Rha in polysaccharide PS-I; and (B) $^1$H-$^{31}$P-HMBC spectrum showing the connection of the glycosyl phosphate to the position number 1 of 3-linked Man and to the position number 6 of the 6-linked Glc in polysaccharide PS-II.
Figure 4:
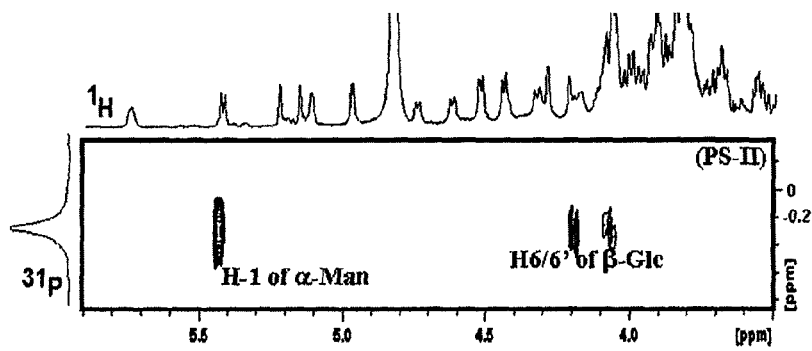

A $^1$H-$^{31}$P HMBC experiment (FIG. 4) afforded $^1$H-$^{31}$P correlations between the $^{31}$P signal at −0.78 ppm and H-1 of A (2-substituted α-Glc) of PS-I and H-4 of C (4-substituted α-Rha) of PS-1 for a sequence of:

... →2)-α-Glc-(1→P→4)-α-Rha-(1→ ....

The results obtained from GC-MS analysis and NMR spectroscopy experiments revealed that *C. difficile* ribotype 027 PS-I was composed of pentaglycosyl phosphate repeating block:

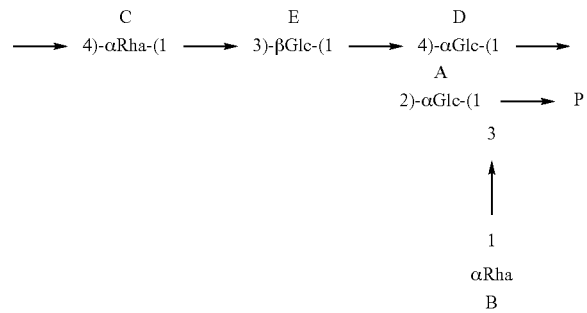

Figure 2:
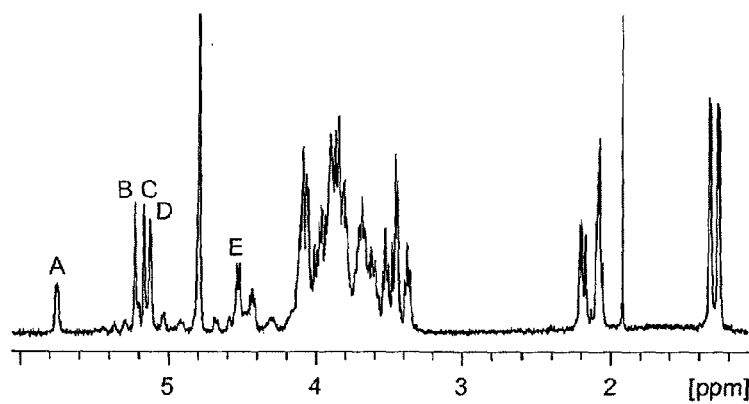
FIG. 2 is a $^1$H-NMR spectrum of (A) PS-I and (B) PS-II.
Figure 2:
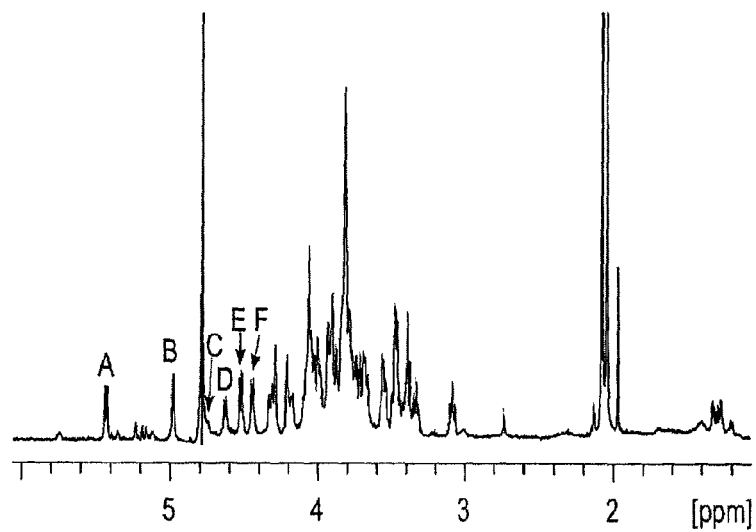
Figure 3:
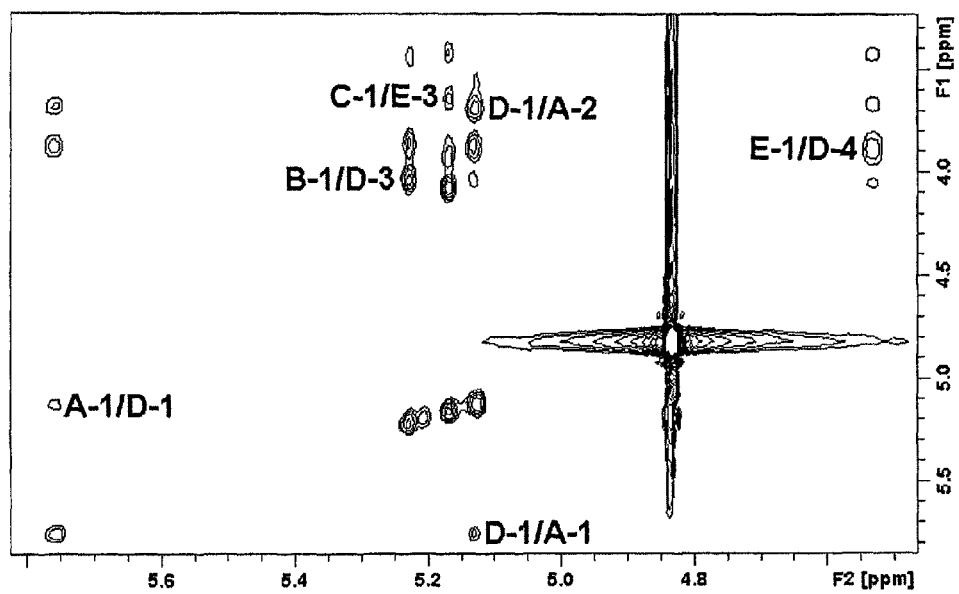
FIG. 3 is a (A) $^1$H-$^1$H NOESY spectrum of *C. difficile* PS-I showing inter-NOE connectivities indicating the sequence of the monosaccharide units, and (B) shows the chemical structure of PS-I repeating saccharide block illustrating the linkages and sequence obtained from the data of the $^1$H-$^1$H NOESY spectrum shown in (A).
Figure 3:
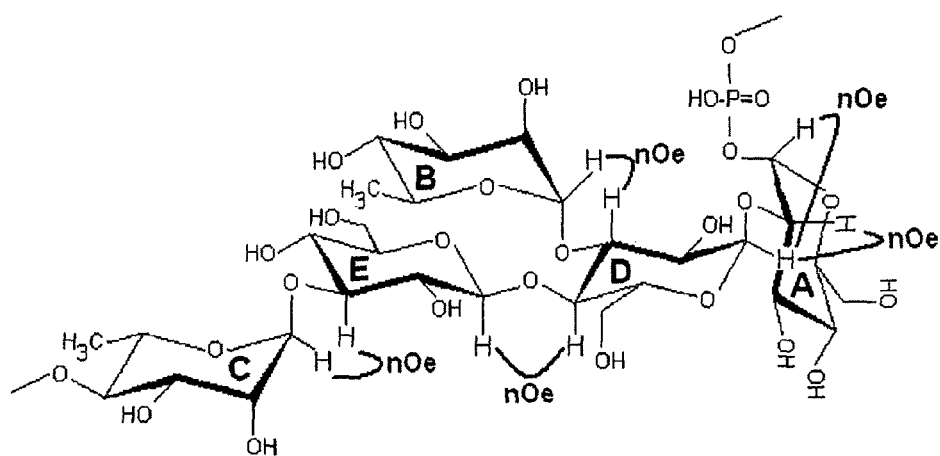

The $^{31}$P-NMR experiments carried out on PS-II revealed that it also carried a monoester phosphate component (no change in chemical shift at higher pH). The 1D $^{31}$P-NMR spectrum of PS-II showed a resonance at $\delta_P$ −1.67 ppm. The $^1$H NMR of PS-II (FIG. 2B) yielded six anomeric resonances, which was also consistent with the number of linkage types present in PS-II. As with PS-I, the sequence of the monosaccharide residues was made possible by 2D NMR experiments that revealed the following sequences:

H-1 (C)/C-3 (A) for [β-GalNAc-(1→3)-α-Man]
H-1 (B)/C-4 (C) for [α-Glc-(1→4)-β-GalNAc]
H-1 (D)/C-4 (B) for [β-GalNAc-(1→4)-α-Glc]
H-1 (E)/C-3 (D) for [β-Glc-(1→3)-β-GalNAc]
H-1 (F)/C-3 (C) for [β-Glc-(1→4)-α-GalNAc]

The $^1$H-$^{31}$P HMBC experiment (FIG. 4) showed that the $^{31}$P signal at −1.67 ppm showed correlations to H-1 of A (3-substituted α-Man) of PS-II and H-6 and 6' of E (6-substituted β-Glc) of PS-II for a sequence of:

... 3)-α-Man-(1→P→6)-β-Glc-(1→ ....

Collectively, the results obtained from GC-MS analysis and NMR spectroscopy experiments revealed that *C. difficile* ribotype 027 PS-II was composed of hexaglycosyl phosphate repeating block:

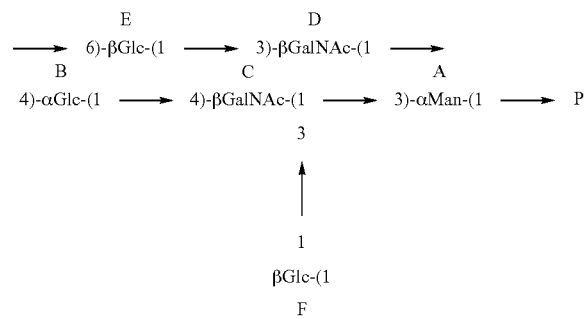

Figure 5:
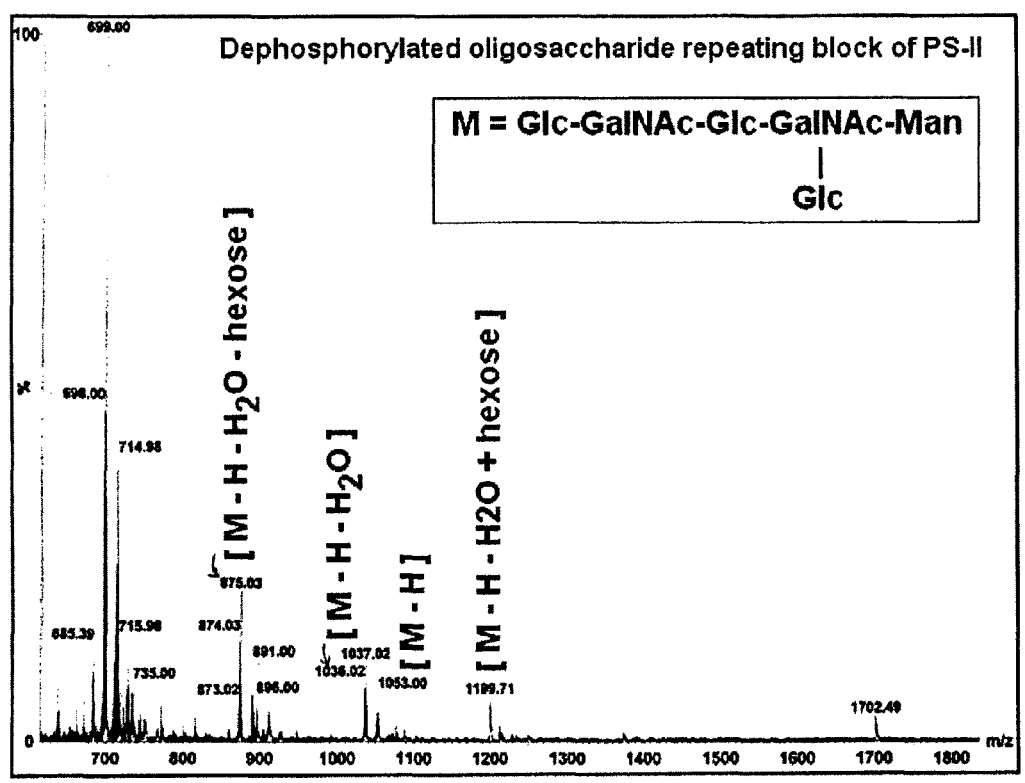
FIG. 5 is a MALDI-TOF mass spectrum of dephosphorylated repeating saccharide of *C. difficile* polysaccharide PS-II.

Matrix-Assisted Laser Desorption Ionization mass spectrometric (MALDI-MS) experiment was used to identify the molecular weight of polysaccharides. The m/z fragments obtained from a dephosphorylated polysaccharide sample identified the molecular weight of the oligosaccharide unit of PS-II to be 1054 Da (FIG. 5). This is consistent with the data obtained by NMR and GC-MS experiments. The MALDI-MS data (FIG. 5) also pointed to the fact, that in some instances, the oligosaccharide repeating block of PS-II may contain an additional hexose unit.

The analysis of PS-II from *C. difficile* MOH 900 and MOH 718 show that they are structurally identical to the PS-II of *C. difficile* ribotype 027.

Figure 7:
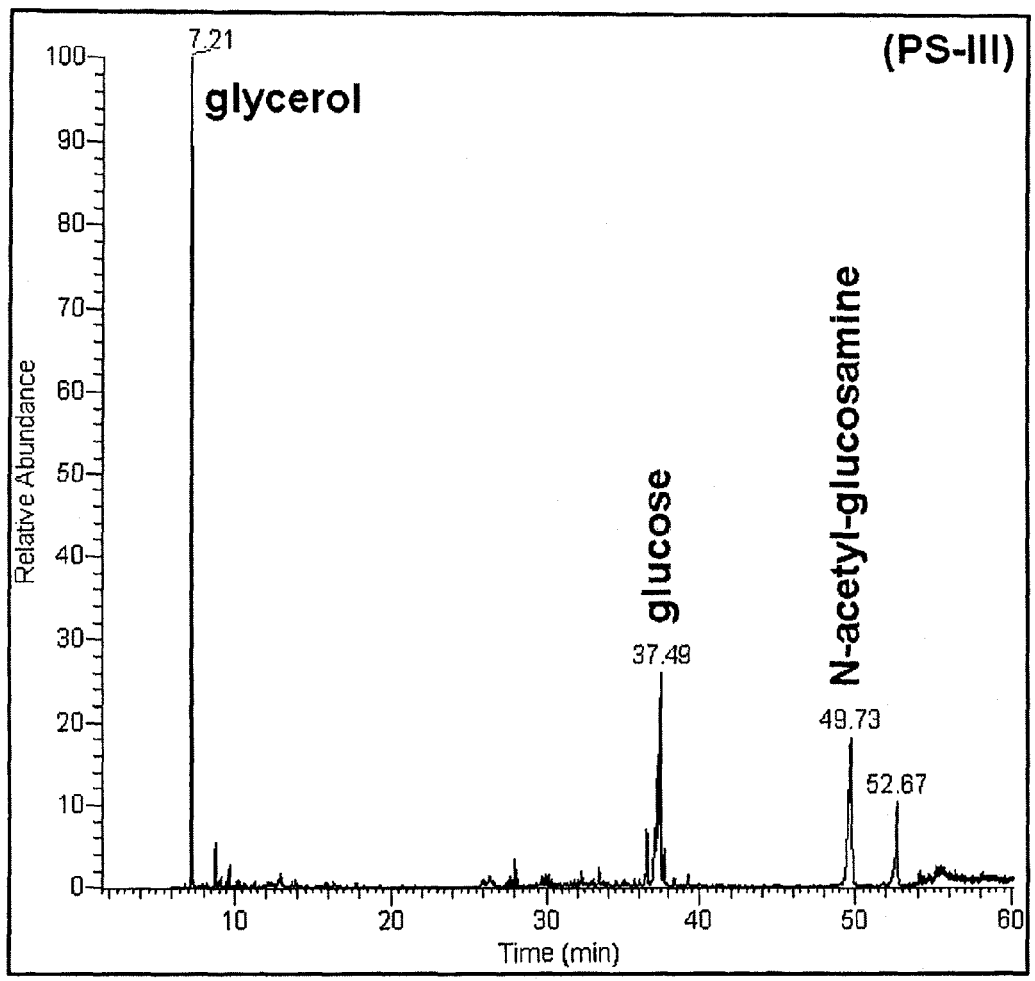
FIG. 7 shows the monosaccharide composition analysis (GC-MS profile) of *C. difficile* polysaccharide PS-Ill.

The chemical, GC-MS and NMR analysis of polysaccharide PS-III that was obtained from the pellet material, was observed to be composed (FIG. 7) of glycerol, glucose, N-acetyl-glucosamine and alditol phosphate.

Figure 8:
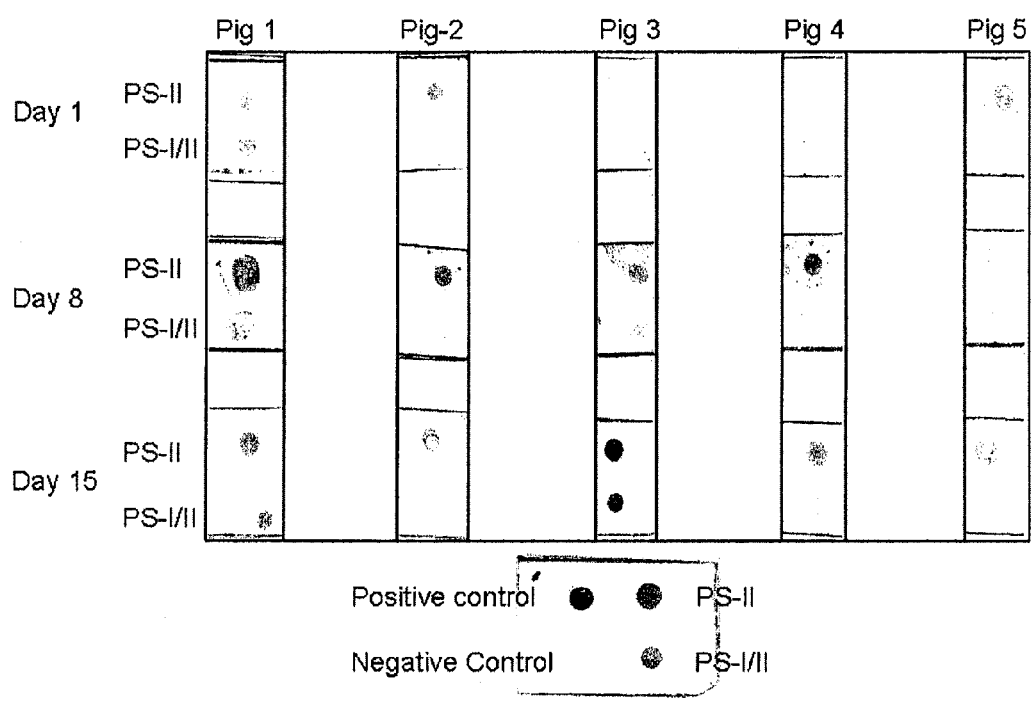
FIG. 8 shows dot-blot serological analysis from five pigs inoculated with a mixture of *C. difficile* cell surface polysaccharides PS-I and PS-II.

Dot-blot serological analysis revealed that the 5 inoculated pigs generated IgM antibodies specific for *C. difficile* PS-II alone, and also for the mixture of PS-I/PS-II (FIG. 8). The data showed that IgM specific for PS-I and PS-I/PS-II increased with a repeated inoculation, and at day 8 and 15 strong immunogenicity was observed, especially for PS-II. No adverse reactions were observed confirming the safety of inoculating with these *C. difficile* PS-I/PS-II cell surface polysaccharides.

Figure 6:
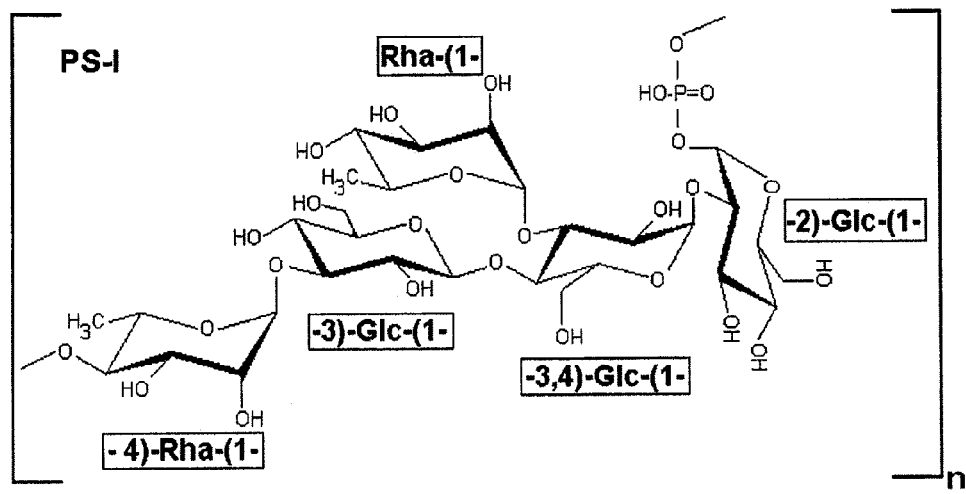
FIG. 6 shows of the covalent chemical structure of the repeating cell surface polysaccharide (A) PS-I and (B) PS-II.
Figure 6:
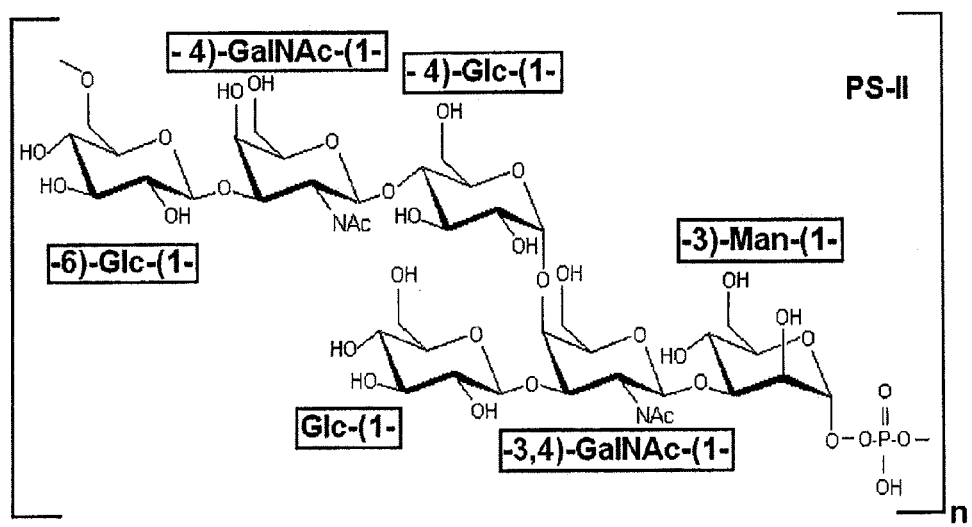

Discussion and Conclusion:

Chemical manipulations in combination with analytical, MS and NMR experiments established the covalent chemical structure of PS-I and PS-II and the composition of PS-III. PS-I (FIG. 6A) was found to consist of a branched pentaglycosyl phosphate repeating unit composed of glycosyl phosphate (P), rhamnose (Rha) and glucose (Glc):

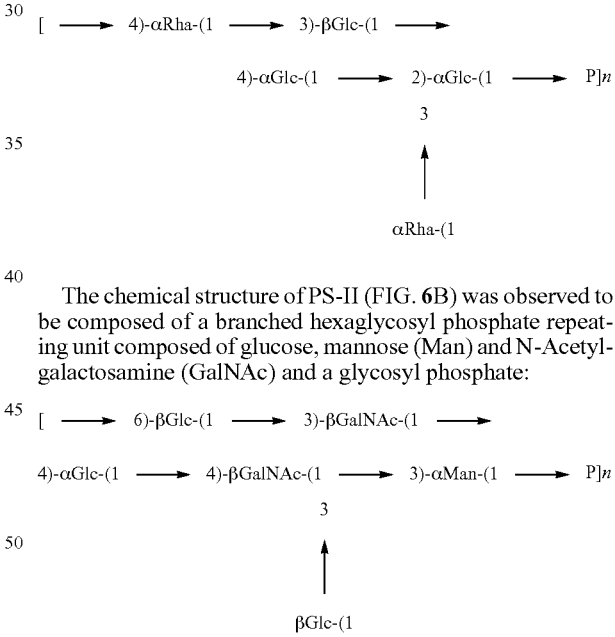

The chemical structure of PS-II (FIG. 6B) was observed to be composed of a branched hexaglycosyl phosphate repeating unit composed of glucose, mannose (Man) and N-Acetyl-galactosamine (GalNAc) and a glycosyl phosphate:

[ → 6)-βGlc-(1 → 3)-βGalNAc-(1 →

4)-αGlc-(1 → 4)-βGalNAc-(1 → 3)-αMan-(1 → P]n

3

↑

βGlc-(1

These findings revealed that *C. difficile* polysaccharide PS-II was expressed by all the *C. difficile* strains investigated here.

The structural results presented here represent the first report describing the covalent chemical structures of *C. difficile* cell-surface polysaccharides and can be the basis for a vaccine preparation.

These novel results represent the first report describing the detailed chemical makeup of *C. difficile* polysaccharides. Here, *C. difficile* ribotype 027 was shown to express at least two structurally variable cell-surface polysaccharides (PS-I and PS-II), each composed of a variety of monosaccharides with several linkage-types. *C. difficile* MOH 900 and MOH 718 were found to express only one type of polysaccharide that has been shown to be structurally similar to PS-II of ribotype 027.

The cell surface polysaccharides PS-I and PS-II of *C. difficile*, were shown to be immunogenic (IgM) in pigs (FIG. 8). PS-II was highly immunogenic and the mixture of PS-I/PS-II was also immunogenic but to a lesser degree.

The purified *Clostridium difficile* cell surface polysaccharides are used as vaccines and/or the glycosyl chains are coupled to a carrier molecule to form an immunologically active glycoconjugate vaccine. The synthesized vaccine will then be used for immunological studies involving animal models.

IV. Prophetic Example(s) of Preparing Conjugates

*C. difficile* cell surface polysaccharides, including PS-I, II and III disclosed in the present application may be coupled to a stable carrier protein, such as for example $CRM_{197}$ and/or Tetanus Toxoid, using coupling techniques known in the art to yield a glycoconjugate vaccine to treat or prevent *C. difficile* infections, or to induce an immune response against *C. difficile*.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

The invention claimed is:

1. An isolated immunogenic *Clostridium difficile* cell surface polysaccharide comprising repeating pentasaccharide units of the formula (I):

(I)

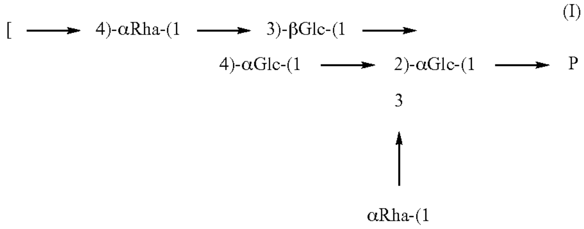

wherein Rha is rhamnose, P is glycosyl phosphate and Glc is glucose or an immunogenic fragment thereof.

2. The cell surface polysaccharide of claim 1, wherein the polysaccharide is a compound of the formula (PS-I):

(PS-I)

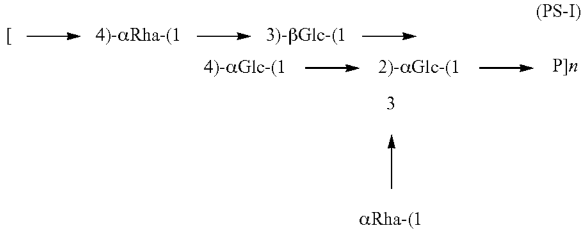

wherein n is an integer from 1-1000, Rha is rhamnose, P is glycosyl phosphate and Glc is glucose or an immunogenic fragment thereof.

3. The cell surface polysaccharide of claim 1, wherein the rhamnose and glucose are present in the pyranose conformation.

4. The cell surface polysaccharide of claim 2, wherein n is an integer from 1 to 100.

5. An Isolated immunogenic *Clostridium difficile* cell surface polysaccharide comprising repeating hexasaccharide units of the formula (II):

(II)

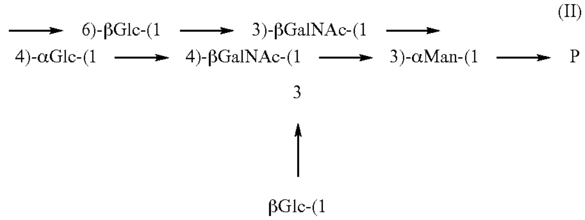

wherein Glc is glucose, GalNAc is N-acetyl-galactosamine, P is glycosyl phosphate and Man is mannose or an immunogenic fragment thereof.

6. The cell surface polysaccharide of claim 5, wherein the polysaccharide is a compound of the formula (PS-II):

(PS-II)

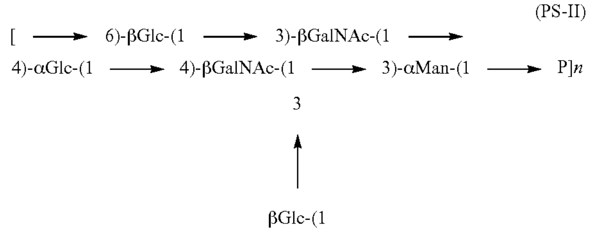

wherein, n is an integer from 1-1000, Glc is glucose, GalNAc is N-acetyl-galactosamine, P is glycosyl phosphate and Man is mannose or an immunogenic fragment thereof.

7. The cell surface polysaccharide of claim 5, wherein the glucose, N-acetyl-galactosamine, and mannose are present in the pyranose conformation.

8. The cell surface polysaccharide of claim 6, wherein n is an integer from 1 to 100.

9. The cell surface polysaccharide of claim 5, wherein the polysaccharide is conjugated to a carrier molecule.

10. The cell surface polysaccharide of claim 9, wherein the carrier molecule is bovine serum albumin, diphtheria toxin mutant $CRM_{197}$, major immunoenhancing protein, Diphtheria toxoid, Tetanus toxoid or proteins derived from *Bordetella*.

11. The cell surface polysaccharide according to claim 5, obtained by growing *Clostridium difficile* bacteria in suitable medium, separating bacterial cells from the medium, extracting cell surface polysaccharides by mild acid treatment under conditions to cleave the polysaccharides from the cell surface material, and purifying the extracted cell surface polysaccharides.

12. A cell surface polysaccharide mixture comprising:

(a) one or more polysaccharides as defined in claim 1; and (b) one or more polysaccharides as defined in claim 5.

13. The cell surface polysaccharide mixture of claim 12, wherein one or more of the polysaccharides are conjugated to a carrier molecule.

14. The cell surface polysaccharide mixture of claim 13, wherein the carrier molecule is bovine serum albumin, diphtheria toxin mutant $CRM_{197}$, major immunoenhancing protein, Diphtheria toxoid, Tetanus toxoid or proteins derived from *Bordetella*.

15. An immunogenic composition comprising the cell surface polysaccharide of claim 5 and a pharmaceutically acceptable excipient, carrier, buffer, stabilizer, or mixtures thereof.

16. An immunogenic composition mixture comprising the cell surface polysaccharide mixture of claim 12 and a pharmaceutically acceptable excipient, carrier, buffer, stabilizer, or mixtures thereof.

17. The immunogenic composition of claim 15, further comprising an adjuvant.

18. A kit comprising the cell surface polysaccharide of claim 1 or the cell surface polysaccharide mixture of claim 12 or the immunogenic composition of claim 15 and instructions for the use thereof.

19. A method of inducing an immune response against *Clostridium difficile* in a subject, comprising administering to said subject an effective amount of the cell surface polysaccharide of claim 1 or the cell surface polysaccharide mixture of claim 18.

20. A method of inducing an immune response against *Clostridium difficile* in a subject, comprising administering to said subject an effective amount of the immunogenic composition of claim 15.

21. The method of claim 19, wherein the subject is a pig, a horse, cattle or a human being.

\* \* \* \* \*

UNITED STATES PATENT AND TRADEMARK OFFICE
CERTIFICATE OF CORRECTION

PATENT NO. : 8,597,663 B2  Page 1 of 1
APPLICATION NO. : 12/676369
DATED : December 3, 2013
INVENTOR(S) : Monteiro et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 762 days.

Signed and Sealed this
Twenty-second Day of September, 2015

Michelle K. Lee
*Director of the United States Patent and Trademark Office*